(12) United States Patent
Friese et al.

(10) Patent No.: US 8,871,964 B2
(45) Date of Patent: Oct. 28, 2014

(54) METHOD FOR CARRYING OUT CHEMICAL REACTIONS WITH THE AID OF AN INDUCTIVELY HEATED HEATING MEDIUM

(75) Inventors: Carsten Friese, Düsseldorf (DE); Andreas Kirschning, Celle (DE); Jürgen Wichelhaus, Wuppertal (DE); Sascha Volkan Ceylan, Hannover (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/447,498

(22) Filed: Apr. 16, 2012

(65) Prior Publication Data

US 2012/0202994 A1    Aug. 9, 2012

Related U.S. Application Data

(63) Continuation of application No. 12/813,653, filed on Jun. 11, 2010, now abandoned, which is a continuation of application No. PCT/EP2008/063763, filed on Oct. 14, 2008.

(30) Foreign Application Priority Data

Dec. 11, 2007   (DE) .................. 10 2007 059 967

(51) Int. Cl.

| | |
|---|---|
| *C07C 205/00* | (2006.01) |
| *H05B 6/10* | (2006.01) |
| *C07C 67/303* | (2006.01) |
| *C07D 295/073* | (2006.01) |
| *C07C 45/69* | (2006.01) |
| *C07D 277/56* | (2006.01) |
| *B01J 8/42* | (2006.01) |
| *C07C 209/36* | (2006.01) |
| *B01J 19/12* | (2006.01) |
| *C07C 205/60* | (2006.01) |
| *C07B 61/00* | (2006.01) |
| *C07C 41/30* | (2006.01) |
| *C07C 67/03* | (2006.01) |
| *C07C 37/055* | (2006.01) |

(52) U.S. Cl.
CPC ................ *B01J 19/12* (2013.01); *H05B 6/106* (2013.01); *C07C 67/303* (2013.01); *C07D 295/073* (2013.01); *C07C 45/69* (2013.01); *C07D 277/56* (2013.01); *B01J 8/42* (2013.01); *C07C 209/36* (2013.01); *C07C 205/60* (2013.01); *B01J 2208/00513* (2013.01); *C07B 61/00* (2013.01); *C07C 41/30* (2013.01); *H05B 6/108* (2013.01); *B01J 2219/00139* (2013.01); *C07C 67/03* (2013.01); *B01J 2208/0038* (2013.01); *C07C 37/055* (2013.01); *B01J 2208/00433* (2013.01)
USPC .......................................................... 560/20

(58) Field of Classification Search
CPC .... C07C 269/06; C07C 69/76; C07C 205/57; C07C 205/56
See application file for complete search history.

(56) References Cited

U.S. PATENT DOCUMENTS

| | | | |
|---|---|---|---|
| 5,110,996 A | 5/1992 | Edwards | |
| 6,110,239 A | 8/2000 | Malone et al. | |
| 7,070,743 B2 * | 7/2006 | Blackwell et al. | ....... 422/186.01 |
| 7,569,624 B2 | 8/2009 | Kolbe et al. | |
| 7,651,580 B2 | 1/2010 | Sauer et al. | |
| 2002/0061588 A1 | 5/2002 | Jacobson et al. | |
| 2002/0119572 A1 * | 8/2002 | Jacobson et al. | .............. 435/466 |
| 2003/0059603 A1 | 3/2003 | Gottfried et al. | |
| 2003/0164371 A1 | 9/2003 | Bergstrom et al. | |

FOREIGN PATENT DOCUMENTS

| | | |
|---|---|---|
| DE | 102005051637 A1 | 5/2007 |
| DE | 102006062651 A1 | 5/2008 |
| EP | 0498998 B1 | 8/1992 |
| JP | 2004250255 A | 9/2004 |
| JP | 2009513327 A | 4/2009 |
| WO | 9521126 A1 | 8/1995 |
| WO | 9901212 A1 | 1/1999 |
| WO | 0038831 A1 | 7/2000 |
| WO | 2006088068 A1 | 8/2006 |

OTHER PUBLICATIONS

Park et al. (J.Am.Chem.Soc., 2006, 128, 7938-7946).*
Furmanek et al. (Acta Biochmica Polonica, 2000, 47(3), 78).*
Park et al. "Local heating of Discrete Droplets Using Magnetic Porous Silicon-Based Photonic Crystals," J. Am. Chem. Soc., vol. 128, 2006, pp. 7938-7946.
F.Schueth et al. "Magnetic nanoparticles Synthesis, stabilization, functionalization and application." Applied Chemistry, Wiley-VCH Verlag GmbH & Co. KGaA, vol. 119, 2007, pp. 1242-1266.
Jansson et al., "Sysnthesis and Reactivityof Laquinimod, a Quinoline-3-carboxmide: Intramolecular Transfer of the Enol Proton to a Nitrogen Atom as a Plausible Mechanism for Ketene Formation," J. Org. Chem., American Chemical Society, 2006, vol. 71, pp. 1658-1667.

* cited by examiner

*Primary Examiner* — Rosalynd Keys
*Assistant Examiner* — Jennifer C Sawyer
(74) *Attorney, Agent, or Firm* — James E. Piotrowski

(57) ABSTRACT

The invention relates to a method for carrying out a chemical reaction for producing a target compound by heating in a reactor a reaction medium containing at least one first reactant, such that a chemical bond inside the first reactant or between the first and a second reactant is formed or modified. The reaction medium is brought into contact with a solid heating medium that can be warmed by electromagnetic induction and that is inside the reactor and is surrounded by the reaction medium. Said heating medium is heated by electromagnetic induction with the aid of an inductor and the target bond is formed from the first reactant or from the first and a second reactant and said target bond is separated from the heating medium.

15 Claims, 4 Drawing Sheets

Manganese ferrite (b):

Bayferrox (c):

FIGURE 2 - Preparation of Catalyst 7:

FIGURE 3 - Preparation of Catalyst 6

FIGURE 4 - Preparation of Catalyst 9
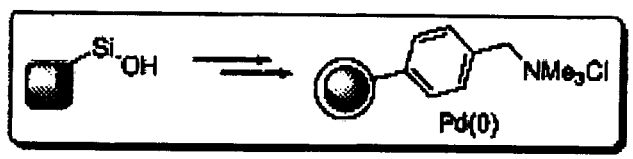
FIGURE 5 - Table 2: Heck-Mizoroki Coupling
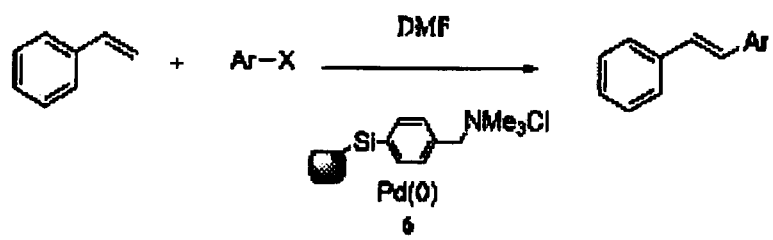
FIGURE 6 - Suzuki-Miyaura Reaction:
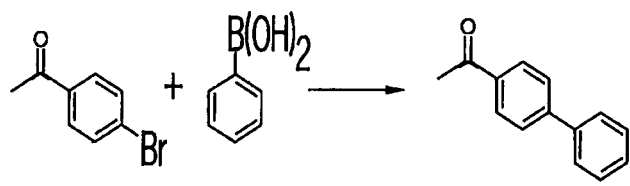
FIGURE 7 - Transesterification of ethyl cinnamate 59 to methyl cinnamate 60.
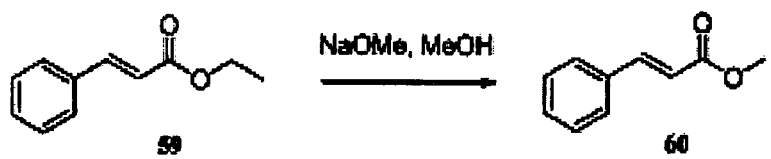

FIGURE 8 - Example 8: Syntheses of Heterocycles:
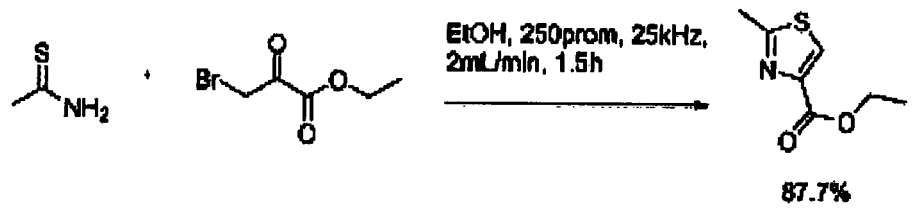
FIGURE 9 - Example 9: Hartwig-Buchwald Coupling:
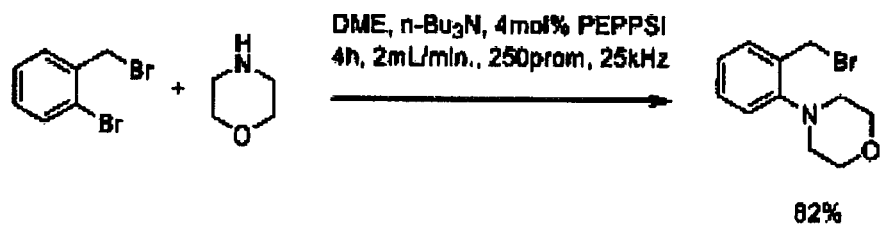
FIGURE 10 - Example 10: Claissen Rearrangement:
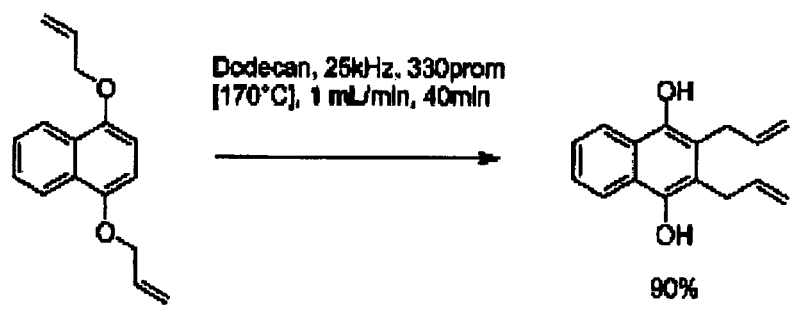
FIGURE 11 - Example 11: Decarboxylation
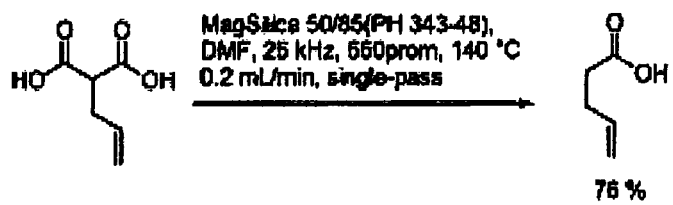

FIGURE 12 - Example 12: Hydrogenation
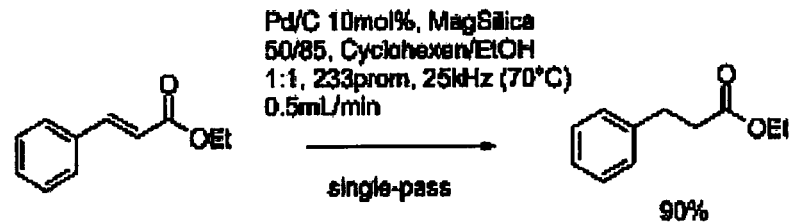
FIGURE 13 - Example 13: Reduction
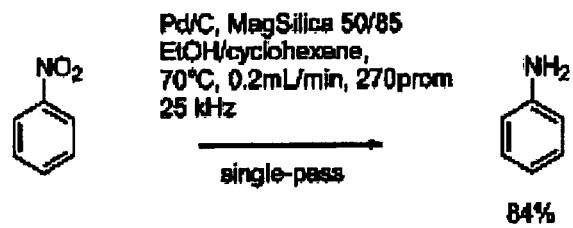
Figure 14 - Example 14: Rearrangement with C-C bond formation
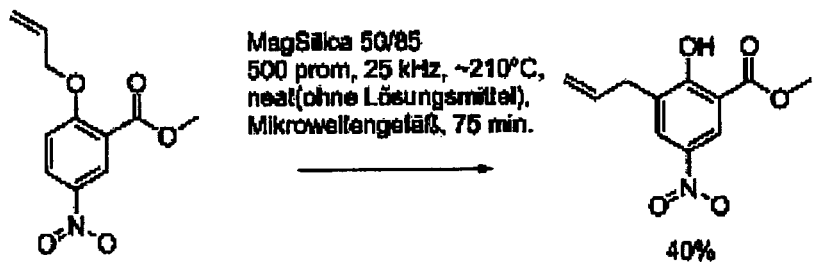

METHOD FOR CARRYING OUT CHEMICAL REACTIONS WITH THE AID OF AN INDUCTIVELY HEATED HEATING MEDIUM

This application is a continuation of U.S. patent application Ser. No. 12/813,653 filed Jun. 11, 2010 which is a continuation of International Patent Application No. PCT/EP2008/063763 filed Oct. 14, 2008, which claims the benefit of German Patent Application No. 10 2007 059 967.8 filed Dec. 11, 2007. The contents of each of the above applications are incorporated herein by reference.

The present invention is in the field of chemical synthesis and relates to a process for carrying out a chemical reaction with the help of an inductively heated heating medium.

In order to carry out thermally inducible chemical reactions, various techniques are known for heating the reactants. Heating by heat conduction is the most widely used. Here the reactants are present in a reactor, wherein either the walls of the reactor are themselves heated or wherein heat-transfer elements, such as for example heating coils or heat exchanger pipes or plates, are built into the reactor. This process is comparatively slow, so that firstly the reactants are heated slowly and secondly the heat input cannot be rapidly suppressed or even compensated for by cooling. An alternative to this consists in heating the reactants by irradiating microwaves into the reactants themselves or in a medium that contains the reactants. However, microwave generators represent a considerable safety risk as they are technically costly and the danger exists for the leakage of radiation.

In contrast to this, the present invention provides a process, in which the reaction medium is heated by bringing it into contact with a heating medium that can be heated by electromagnetic induction and which is heated "from the exterior" by electromagnetic induction with the aid of an inductor.

The process of inductive heating has been used for some time in industry. The most frequent applications are melting, curing, sintering and the heat treatment of alloys. However, processes such as gluing, shrinking or bonding of components are also known applications of this heating technology.

Processes for the isolation and analysis of biomolecules are known from the German patent application DE 198 00 294, wherein the biomolecules are bonded onto the surface of inductively heatable magnetic particles. This document states: "The principle of operation consists in adsorptively or covalently binding biomolecules to the surface of a functional polymer matrix, in which the inductively heatable magnetic colloids or finely dispersed magnetic particles are encapsulated, said biomolecules being capable of binding analytes such as e.g. DNA/RNA sequences, antibodies, antigens, proteins, cells, bacteria, viruses or fungal spores according to the complementary affinity principle. Once the analytes have been bound to the matrix the magnetic particles can be heated in a high frequency magnetic alternating field to temperatures of preferably 40 to 120° C. that are relevant for analysis, diagnostics and therapy." Furthermore, this document treats the technical design of rinsing systems and high frequency generators, which can be used in this process. The cited document thus describes the use of inductively heatable particles for the analysis of complex biological systems or biomolecules.

DE 10 2005 051637 describes a reactor system with a microstructured reactor as well as a process for carrying out a chemical reaction in such a reactor. Here the reactor as such is heated by electromagnetic induction. The heat transfer into the reaction medium results through the heated reactor walls. On the one hand, this limits the size of the surface that is available for heating the reaction medium. On the other hand, parts of the reactor that are not in direct contact with the reaction medium also need to be heated.

U.S. Pat. No. 5,110,996 describes the preparation of vinylidene fluoride by the gaseous phase reaction of dichlorodifluoromethane with methane in a heated reactor. The reactor was filled with a non-metallic filler. A metallic hull that is heated from the exterior by electromagnetic induction surrounds the reaction chamber that contains this filler. The reaction chamber itself is therefore heated from the exterior, whereby the filler is likewise heated over time by radiating heat and/or thermal conductivity. A direct heating of the filler circulated by the reactants does not occur if this filler is electrically conductive, as the metallic reactor wall shields the electromagnetic fields from the induction coil.

WO 95/21126 discloses a gas phase process for preparing hydrogen cyanide from ammonia and a hydrocarbon with the aid of a metallic catalyst. The catalyst is inside the reaction chamber so that reactants circulate round the catalyst. It is heated from the exterior by electromagnetic induction with a frequency of 0.5 to 30 MHz, i.e. with a high frequency alternating field. In regard to this, this document cites the previously cited document U.S. Pat. No. 5,110,996 with the remark that normally, inductive heating is carried out in the frequency range from about 0.1 to 0.2 MHz. However, this indication is not comprised in the cited U.S. Pat. No. 5,110,996, and it is unclear what it refers to.

WO 00/38831 is concerned with controlled adsorption and desorption processes, wherein the temperature of the adsorber material is controlled by electromagnetic induction.

BRIEF DESCRIPTION OF THE DRAWINGS

Referring now to the drawings wherein like elements are numbered alike in the several

FIGURES

Figure 1:
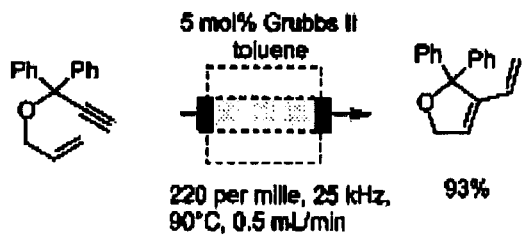
Figure 1:
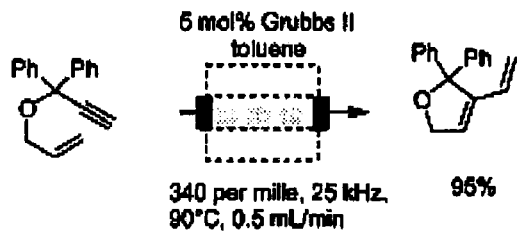
Figure 1:
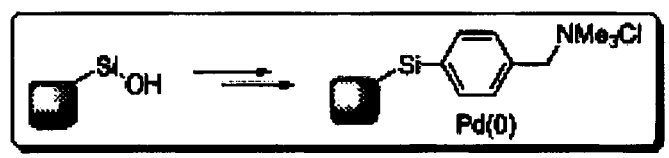
Figure 1:
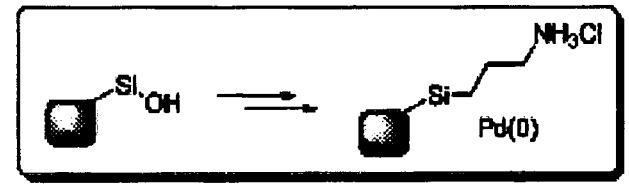

FIG. 1 shows reactions carried out with different heating media.
FIG. 2 shows the preparation of Catalyst 7.
FIG. 3 shows the preparation of Catalyst 6.
FIG. 4 shows the preparation of Catalyst 9.
FIG. 5 shows Heck-Mizoroki Coupling.
FIG. 6 shows Suzuki-Miyaura Reaction.
FIG. 7 shows transesterification of ethyl cinnamate 59 to methyl cinnamate 60.
FIG. 8 shows synthesis of heterocycles.
FIG. 9 shows Hartwig-Buchwald coupling.
FIG. 10 shows Claissen rearrangement.
FIG. 11 shows decarboxylation.
FIG. 12 shows hydrogenation.
FIG. 13 shows reduction.
FIG. 14 shows rearrangement with C—C bond formation.

The subject matter of the present invention is a process for carrying out a chemical reaction for producing a target compound by heating a reaction medium comprising at least one first reactant in a reactor, whereby a chemical bond within the first reactant or between the first and a second reactant is formed or modified, wherein the reaction medium is brought into contact with a solid heating medium that can be heated by electromagnetic induction and that is inside the reactor and is surrounded by the reaction medium, and said heating medium is heated by electromagnetic induction with the aid of an inductor, wherein the target compound is formed from the first reactant or from the first and a second reactant and wherein said target compound is separated from the heating medium.

Accordingly, the chemical reaction takes place by heating a reaction medium that comprises at least one first reactant. This includes the possibility that the reaction medium, for example a liquid, is itself involved in the reaction and therefore represents a reactant. The whole of the reaction medium can therefore consist of one reactant. Further, a reactant can be dissolved or dispersed in the reaction medium, wherein the reaction medium can itself be inert or can represent for its part a reactant. Or one, two or more reactants are dissolved or dispersed in a reaction medium that is itself not changed by the chemical reaction.

In this regard the reaction medium can consist of a single reactant or comprise it, wherein reactant molecules react with one another or wherein a modification of the chemical bonding system can occur in the individual molecules of the reactant itself. The reactant is chemically modified in both cases. In the general case, however, two or more reactants participate with one another in reaction, wherein chemical bonds within and/or between the individual reactants are rearranged or formed.

The solid heating medium is surrounded by the reaction medium. This can mean that the solid heating medium, apart from possible peripheral zones, is present within the reaction medium, e.g. when the heating medium is present in the form of particles, filings, wires, gauze, wool, packing materials etc. However, this can also mean that the reaction medium flows through the heating medium through a plurality of cavities in the heating medium, when for example the latter consists of one or more membranes, a bundle of pipes, a rolled up metal foil, frits, porous packing materials or from a foam. In this case the heating medium is also essentially surrounded by the reaction medium, as the majority of its surface (90% or more) remains in contact with the reaction medium. In contrast to this is a reactor, whose external wall is heated by electromagnetic induction (such as for example that cited in the document U.S. Pat. No. 5,110,996), where only the inner reactor surface comes into contact with the reaction medium.

The wall of the reactor is made of a material that neither shields nor absorbs the electromagnetic alternating field produced by the inductor and therefore is itself not heated up. Consequently, metals are unsuitable. For example it can consist of plastic, glass or ceramics (such as for example silicon carbide or silicon nitride). The last mentioned is particularly suitable for reactions at high temperatures (500-600° C.) and/or under pressure.

The above-described method has the advantage that the thermal energy for carrying out the chemical reaction is not brought into the reaction medium through surfaces such as for example the reactor walls, heating coils, heat exchange plates or the like, but rather is produced directly in the volume of the reactor. The ratio of heated surface to volume of the reaction medium can, in this case, be considerably greater than for a heating through heat transfer surfaces, as is also the case, for example, cited in DE 10 2005 051637 in the introduction. In addition to this, the degree of efficiency of electrical current to thermal output is improved. By switching on the inductor, the heat can be generated in the totality of the solid heating medium, which remains in contact through a very high surface with the reaction medium. Switching off the inductor very quickly suppresses any further thermal input. This permits a very targeted reaction control.

After the target compound is formed it is separated from the heating medium. In the best case the target compound is isolated in pure form, i.e. free of solvent and with no more than the usual impurities. However, the target compound can also be separated from the heating medium in a mixture with reactants or as a solution in the reaction mixture and then be isolated by further working up or be transferred into another solvent, as is desired. The process is therefore suitable for the preparative manufacture of the target compound in order to be able to use these in a further step.

In contrast to this are processes, in which a chemical reaction is indeed likewise initiated by electromagnetic induction of a heating medium, but the reaction does not serve to prepare a target compound that is separated from the heating medium after the end of the reaction. An example of this is the curing of resin systems, wherein the curing reaction is initiated on particles that are dispersed in the resin system and which are heated by electromagnetic induction. In such a case the particles remain in the cured resin system and no defined target compound is isolated. The same is true for the opposite case, in which an adhesive compound is unglued again by the inductively heated particles that are present in the adhesive matrix. A chemical reaction can indeed occur in this case, but no target compound is isolated.

The heating medium consists of an electrically conductive material that is heated by the action of an alternating electrical field. It is preferably selected from materials that possess a very high surface to volume ratio. For example the heating medium can be selected in each case from electrically conductive filings, wires, meshes, wool, membranes, porous frits, pipe bundles (of three or more pipes), rolled up metal foils, foams, packing materials such as for example granules or pellets, Raschig rings and particularly particles that preferably have an average diameter of not more than 1 mm. For example, mixed metallic elements can be employed as the heating medium, as are used for static mixers. In order to be heatable by electromagnetic induction, the heating medium is electrically conductive, for example metallic (wherein it can be diamagnetic) or it exhibits enhanced interaction towards diamagnetism with a magnetic field and in particular is ferromagnetic, ferrimagnetic, paramagnetic or superparamagnetic. In this regard it is immaterial whether the heating medium is of an organic or inorganic nature or whether it contains both inorganic as well as organic components.

In a preferred embodiment, the heating medium is selected from particles of electrically conductive and/or magnetizable solids, wherein the mean particle size of the particles is from 1 to 1000, especially from 10 to 500 nm. The mean particle size and when necessary also the particle size distribution can be determined for example by light scattering. Magnetic particles are preferably selected, for example ferromagnetic or superparamagnetic particles, which exhibit the lowest possible remanence or residual magnetism. This has the advantage that the particles do not adhere to each other. The magnetic particles can be in the form of "ferrofluids", i.e. liquids, in which nanoscale ferromagnetic particles are dispersed. The liquid phase of the ferrofluid can then serve as the reaction medium.

Magnetizable particles, in particular ferromagnetic particles, which exhibit the desired properties, are known from the prior art and are commercially available. The commercially available ferrofluids may be cited. Examples for the manufacture of magnetic nano-particles, which can be used in the context of the inventive process, can be found in the article by Lu, Salabas and Schüth: "Magnetische nano-Partikel: Synthese, Stabilisierung, Funktionalisierung and Anwendung", Angew. Chem. 2007, 119, pp. 1242 to 1266.

Suitable nano-particles with different compositions and phases are known. The following examples may be cited: pure metals such as Fe, Co and Ni, oxides such as $Fe_3O_4$ and gamma-$Fe_2O_3$, spinel type ferromagnets such as $MgFe_2O_4$, $MnFe_2O_4$ and $CoFe_2O_4$ as well as alloys such as $CoPt_3$ and FePt. The magnetic nano-particles can be of a homogeneous structure or can possess a core-shell structure. In the latter case the core and shell can consist of different ferromagnetic or even antiferromagnetic materials. However, embodiments are also possible, in which a magnetizable core that can be for example ferromagnetic, antiferromagnetic, paramagnetic or superparamagnetic, is surrounded by a non-magnetic material. An organic polymer for example, can represent this material. Or the shell consists of an inorganic material such as for example silica or $SiO_2$. A coating of this type can prevent a chemical interaction between the reaction medium or the reactants with the material of the magnetic particle itself. In addition, the shell material can be surface modified, without the material of the magnetizable core interacting with the functionalizing entity. In this regard, a plurality of particles of the core material can be enclosed together into a shell of this type.

Nano-scale particles of superparamagnetic substances for example can be employed as the heating medium and are selected from aluminum, cobalt, iron, nickel or their alloys, metal oxides of the type n-maghemite (gamma-$Fe_2O_3$), n-magnetite ($Fe_3O_4$) or ferrites of the type $MeFe_2O_4$, wherein Me is a divalent metal selected from manganese, copper, zinc, cobalt, nickel, magnesium, calcium or cadmium. Preferably the mean particle size of these particles is <100 nm, preferably <=51 nm and particularly preferably <30 nm.

An exemplary suitable material is available from Evonik (formally Degussa) under the name MagSilica®. In this material, iron oxide particles having a size between 5 and 30 nm are embedded in an amorphous silica matrix. Such iron oxide-silicon dioxide composite particles, which are described in more detail in the German patent application DE 101 40 089, are particularly suitable.

These particles can comprise superparamagnetic iron oxide domains with a diameter of 3 to 20 nm. This is understood to mean superparamagnetic regions that are spatially separated from one another. The iron oxide can be present in these domains in a single modification or in various modifications. A particularly preferred superparamagnetic iron oxide domain is gamma-$Fe_2O_3$, $Fe_3O_4$ and mixtures thereof.

The content of the superparamagnetic iron oxide domains of these particles can be between 1 and 99.6 wt. %. The individual domains are separated from one another and/or surrounded by a non-magnetizable silicon dioxide matrix. The region containing a content of the superparamagnetic iron oxide domains is preferably >30 wt. %, particularly preferably >50 wt. %. The achievable magnetic effect of the inventive particle also increases with the content of the superparamagnetic regions. The silicon dioxide matrix also stabilizes the oxidation level of the domain in addition to separating the spatial separation of the superparamagnetic iron oxide domains. Thus, for example, magnetite is stabilized as the superparamagnetic iron oxide phase by a silicon dioxide matrix. These and further properties of these particles that are particularly suitable for the present invention are listed in more detail in DE 101 40 089 and in WO 03/042315.

Furthermore, nano-scale ferrites such as those known for example from WO 03/054102 can be employed as the heating medium. These ferrites possess the composition $(M^a_{1-x-y} M^b_x Fe^{II}_y) Fe^{III}_2 O_4$, in which
$M^a$ is selected from Mn, Co, Ni, Mg, Ca, Cu, Zn, Y and V,
$M^b$ is selected from Zn and Cd,
x stands for 0.05 to 0.95, preferably 0.01 to 0.8,
y stands for 0 to 0.95 and
the sum of x and y is maximum 1.

The particles that can be heated by electromagnetic induction can represent the heating medium without any additional additives. However, it is also possible to mix the particles that can be heated by electromagnetic induction with other particles that cannot be heated by electromagnetic induction. Sand for example can be used. Accordingly, the inductively heatable particles can be diluted with non-inductively heatable particles. This allows an improved temperature control. In another embodiment, the inductively heatable particles can be admixed with non-inductively heatable particles that have catalytic properties for the chemical reaction to be carried out or that participate in other ways in the chemical reaction. These particles are then not directly heated by electromagnetic induction, but rather indirectly, in that they are heated by contact with the heatable particles or by heat transfer from the reaction medium.

If nano-scale electromagnetically inductively heatable particles are blended with coarser non-inductively heatable particles, then this can lead to a decreased packing density of the heating medium. In embodiments, in which the reaction medium flows through a packing made of the heating medium, this can result in a desired reduction of the pressure drop in the flow-through reactor.

The solid heating medium can be surface-coated with a substance that is catalytically active for the desired chemical reaction. For example these can be organic molecules or biomolecules having an enzymatic action. In this case care should be taken to ensure that the heating medium is not heated too strongly to cause these molecules to lose their enzymatic action.

In particular, the inductively heatable heating medium can be coated with metal atoms or metallic compounds, whose catalytic activity is known. For example, atoms or compounds of metals can be of the lanthanide series, especially Sm or Ce, Fe, Co, Ni or precious metals, preferably platinum metals and especially Pt or Pd.

Particles that comprise magnetizable domains in a silicon dioxide matrix or silica matrix, for example the composite particles of iron oxide and silicon dioxide that are described above, are particularly suitable for coating with catalytically active atoms or compounds. The silicon dioxide shell carries, as is described in more detail in WO 03/042315, reactive OH groups, whose reactivity can be exploited in order to fix the catalytically active substance to the particle surface. Some examples of this are presented in the experimental part.

In principle the chemical reaction can be carried out in a continuous or batch manner. If the reaction is carried out in a batch mode, then the reactive medium and the inductively heated solid heating medium preferably move relative to one another during the reaction. When using a particulate heating medium this can be effected in particular by stirring the reaction mixture with the heating medium or by swirling the heating medium in the reaction medium. If for example meshes or wool are used in a filiform shaped heating medium, then the reaction vessel that contains the reaction medium and the heating medium can be shaken.

A preferred embodiment of a batch mode reaction consists in the reaction medium being present together with particles of the heating medium in a reaction vessel, and is moved with the help of a moving element located in the reaction medium, wherein the moving element is arranged as the inductor, by which the particles of the heating medium are heated by electromagnetic induction. Consequently, in this embodiment the inductor is found inside the reaction medium. The moving element can be designed for example as a stirrer or as a plunger that moves back and forth.

Provision for externally cooling the reactor during the chemical reaction can also be made. This is possible in particular for batch modes if, as described above, the inductor is immersed in the reaction medium. The supply of the electromagnetic alternating field into the reactor is then not impeded by the cooling apparatus.

The reactor can be cooled from inside by cooling coils or heat exchangers or preferably from outside. Optionally precooled water or even a coolant for example whose temperature is below 0° C. can be used for cooling. Exemplary coolants of this type are ice-table salt mixtures, methanol/dry ice or liquid nitrogen. The cooling creates a temperature gradient between the reactor wall and the inductively heated heating medium. This is particularly pronounced when a coolant with a temperature significantly below 0° C. is used, for example methanol/dry ice or liquid nitrogen. The reaction medium that is heated by the inductively heated heating medium is then externally cooled down again. In this case the chemical reaction of the reactants then only occurs when it is in contact with the heating medium or is at least in its direct proximity. Due to the relative movement of the reaction medium to the heating medium, products formed during the reaction rapidly reach cooler regions of the reaction medium, such that their thermal subsequent reaction is inhibited. In this way, a desired reaction path can be kinetically selected when a plurality of possible reaction paths of the reactant(s) exist.

In an alternative embodiment, the chemical reaction is carried out continuously in a flow-through reactor that is at least partially filled with the solid heating medium and thereby possesses at least one heating zone that can be heated by electromagnetic induction, wherein the reaction medium flows continuously through the flow-through reactor and wherein the inductor is located outside the reactor. Here the reaction medium flows round the heating medium, e.g. when this is in the form of particles, filings, wires, meshes, wool, packing materials etc. Or the reaction medium flows through the heating medium through a plurality of cavities in the heating medium, when this consists for example of one or a plurality of membranes, frits, porous packing materials or a foam.

The flow-through reactor is preferably designed as a tubular reactor. In this case the inductor can totally or at least partially surround the reactor. The electromagnetic alternating field generated by the inductor is then fed from all sides or at least from a plurality of places into the reactor.

"Continuously" is hereby understood to mean as usual a reaction mode, in which the reaction medium flows through the reactor in at least such a period of time that a total volume of reaction medium that is large in comparison with the internal volume of the reactor itself has flowed through the reactor, before the flow of reaction medium is discontinued. "Large" in this context means: "at least twice as large". Naturally, a continuously operated reaction of this type also has a beginning and an end.

In this continuous process in a flow-through reactor it is possible for the reactor to have a plurality of heating zones. The different heating zones can be differently heated for example. This can be the result of arranging different heating media in the flow-through reactor or due to differently mounted inductors along the reactor.

The use of at least two heating zones constitutes a particular embodiment, in that the flow-through reactor possesses a first and a second heating zone, wherein the first heating zone in the flow direction of the reaction medium does not comprise a heating medium loaded with a catalytically active substance, whereas the second heating zone in the flow direction of the reaction medium does comprise a heating medium loaded with a catalytically active substance. In an alternative embodiment, the opposite arrangement is chosen for the catalytically and non-catalytically active heating medium. This allows an additional non-catalytically initiated reaction step to be carried out prior to or after a catalytically active reaction step.

The solvent or the reaction medium can also be initially preheated in a conventional manner prior to its contacting the heating medium in the reaction.

When required, a cooling zone, for example in the form of a cooling jacket around the reactor, can be provided after the (last) heating zone.

Furthermore, after leaving the heating zones the reaction medium can be brought into contact with an absorbing substance that removes by-products or impurities from the reaction medium. For example it can be a molecular sieve, through which flows the reaction medium after having left the heating zones. In this way the product can be purified immediately after its production.

Depending on the chemical reaction rate, the product yield can optionally be increased by at least partially recycling the reaction medium that has flowed through the solid heating medium back through the solid heating medium again. In this way the impurities, by-products or even the desired major product can be removed from the reaction medium after each passage through the solid heating medium. The various known separation methods are suitable for this, for example absorption on an absorbing substance, separation through a membrane process, precipitation by cooling or separation by distillation. This ultimately enables a complete conversion of the reactant(s) to be achieved. This is also true in cases where without separating the reaction product the chemical reaction only proceeds to an equilibrium state.

The required total contact time of the reaction medium with the inductively heated heating medium needs to be chosen as a function of the kinetics of each chemical reaction. The slower the desired chemical reaction, the longer the contact time. This has to be empirically adjusted for each individual case. As a guide, the reaction medium preferably flows once or a plurality of times through the flow-though reactor with a speed such that the total contact time of the reaction medium with the inductively heated heating medium is in the range of one second to 2 hours prior to separating the target product. Shorter contact times are conceivable but more difficult to control. Longer contact times can be required for particularly slow chemical reactions, but increasingly worsen the economics of the process.

Independently of whether the reaction is run batch wise or continuously in a flow-through reactor, the reactor can be designed as a pressure reactor and the chemical reaction is carried out at a pressure greater than atmospheric pressure, preferably under at least 1.5 bar. It is well known that the product yield can be increased in this way when the product formation (formation of the target compound) is associated with a volume reduction. For two or more possible reactions, the formation of that particular product can be preferred that results in the greatest reduction in volume.

The inventive process is preferably carried out in such a way that the reaction medium in the reactor is in liquid form under the set reaction conditions (particularly temperature and pressure). This generally makes possible, based on the reactor volume, better volume/yields over time than for gas phase reactions.

The nature of the heating medium and the design of the inductor are matched to each other in such a way to permit the reaction medium to be heated up. A critical variable for this is firstly the rated power of the inductor in watts as well as the frequency of the alternating field generated by the inductor. In principle, the greater the mass of the heating medium to be inductively heated, the higher will be the chosen power. In practice, the achievable power is limited primarily by the ability to cool the generator required for supplying the inductor.

Particularly suitable inductors generate an alternating field with a frequency in the range of about 1 to about 100 kHz, preferably from 10 to 80 kHz and particularly preferably from about 10 to about 30 kHz. Inductors of this type together with the associated generators are commercially available, for example from IFF GmbH in Ismaning (Germany).

Thus the inductive heating is preferably carried out with an alternating field in the medium frequency range. This has the advantage, when compared with an excitation with higher frequencies, for example with those in the high frequency range (frequencies above 0.5, especially above 1 MHz), that the energy input into the heating medium can be better controlled. This is particularly true when the reaction medium is in liquid form under the reaction conditions. Consequently, in the context of the present invention the reaction medium is preferably in liquid form and inductors are employed that generate an alternating field in the abovementioned medium frequency range. This permits an economic and well controllable reaction process.

In a special embodiment of the inventive process, the heating medium is ferromagnetic and exhibits a Curie temperature in the range of about 40° C. to about 250° C., and is selected such that the Curie temperature does not differ by more than 20° C., preferably by not more than 10° C. from the selected reaction temperature. This affords an inherent protection against an unintended overheating. The heating medium can be heated by electromagnetic induction only up to its Curie temperature; it will not be heated any further above this temperature by the electromagnetic alternating field. Even with a malfunction of the inductor, the temperature of the reaction medium is prevented from any unintentional increase to a value significantly above the Curie temperature of the heating medium. Should the temperature of the heating medium fall below its Curie temperature then it will again be heated by electromagnetic induction. This leads to a self-regulation of the temperature of the heating medium in the region of the Curie temperature.

The inventive process is particularly suitable for carrying out thermally induced reactions. In principle there is no limit to the possible reaction types—with the proviso that neither reaction conditions (such as for example pH) nor educts are chosen that could destroy the heating medium. For example, chemical reactions can be carried out in which at least one chemical bond between two carbon atoms or between a carbon atom and an atom X is formed, cleaved or rearranged, wherein X is selected from: H, B, O, N, S, P, Si, Ge, Sn, Pb, As, Sb, Bi and halogens. The reaction can also involve a rearrangement of chemical bonds, such as occurs for example in cycloadditions and Diels-Alder reactions. For example, the thermally induced reaction can correspond to at least one of the following reaction types: oxidation, reduction (including hydrogenation), fragmentation, addition to a double or triple bond (incl. cycloaddition and Diels-Alder reactions), substitution ($SN_1$ or $SN_2$, radical), especially aromatic substitution, elimination, rearrangement, cross coupling, metathetical reactions, formation of heterocycles, ether formation, ester formation or transesterification, amine or amide formation, urethane formation, pericyclic reactions, Michael addition, condensation, polymerization (radical, anionic, cationic), polymer grafting.

For reduction or hydrogenation reactions, suitable reducing agents or hydrogen sources are for example: cycloalkenes such as cyclohexene, alcohols such as ethanol, inorganic hydrogenation reagents such as sodium borohydride or sodium aluminum hydride.

Fats or oils for example can be fragmented. This can occur in solution, but also in the substance in the absence of solvent. In the latter case the fat or oil as such represents the whole reaction medium.

Reactions, which lead to inorganic target products, are also possible of course.

The following examples exemplify chemical reactions on a laboratory scale that were carried out with the inventive process in a flow-through reactor. The present invention is of course not limited to these.

EXAMPLES

The invention was tested on a laboratory scale. Glass tubes (10 cm long) and of varying inner and outer diameters were used as the tubular reactors. The tubes were provided with screw connections on both ends so as to be able to attach the HPLC and suitable tubing.

The inductor that was used had the following performance characteristics: inductivity: 134 μHenry, winding count for the spool: =2–16, cross sectional area=2.8 mm2 (the cross sectional area results from the number of the conductor wires in the inductor and their diameter.) The diameter of the gap for receiving the tubular reactor was 12 mm. For all experiments the inductor was operated with a frequency of 25 kHz.

In the experiments the specified frequency of 25 kHz was left constant and the heating control was undertaken solely through the PWM (PWM=on/off switch for a square wave signal at a fixed fundamental frequency). In the following the PWM is stated in ‰. The induced temperature was measured with a thermocouple and an infrared thermometer. The thermocouple was mounted directly behind the reactor in the fluid so as to permit an accurate as possible measurement. However, due to the metallic components of the thermocouple, a minimum distance of 4 cm had to be observed. A laser infrared thermometer with close focus optics was used for the second temperature measurement. The measurement point had a diameter of 1 mm. With this method the surface temperature of the reactor should be measured in order to obtain a second measurement point for the temperature determination. The emission factor of the material is an important constant for an infrared measurement. It is a measure of the heat emission. An emission factor of 0.85 was used and corresponds to that of an average glass.

Heating tests with different heating media:

The experiments were carried out at a frequency of 25 kHz with an EW5 unit (power 5 watts) with dry powders (no flow). Each heating time lasted for 10 minutes and the temperature was measured with a pyrometer. The following heating media were tested:

a) MagSilica® 58/85 from Evonik (formerly Degussa), b) Manganese ferrite powder from SusTech GmbH, Darmstadt, c) Bayferrox® 318 M: synthetic alpha-$Fe_3O_4$ from Harald Scholz & Co. GmbH, d) Manganese-zinc-ferrite, surface coated with oleic acid, ferrite content 51.7 wt. %, SusTech GmbH, Darmstadt After 10 minutes the following temperatures were reached:

| Sample | PWM = 300 ‰ | PWM = 400‰ |
|---|---|---|
| a) | 170° C. | 220° C. |
| b) | 130° C. | 150° C. |
| c) | 70° C. | 150° C. |
| d) | 60° C. | 65° C. |

Reactions Carried Out with Different Heating Media:

In each case the reactor was filled with 3.3 g of the cited material in order to obtain the desired heating by the inductor for the reactions. The reactions are shown in FIG. 1.

In addition, the heating of rolled copper foil by electromagnetic induction was examined: The foil was heated at a frequency of 20 kHz and a PWM of only 175‰ after less than 10 minutes to >160° C.

The heating medium for the following experiments was Magsilica 58/85 from Evonik (formerly Degussa) and was optionally surface modified according to the following process. The icon

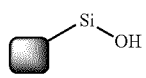

represents MagSilica, and the icon

represents a MagSilica residue after reaction, in the following reaction schemes.

Surface modification of the heating medium with catalysts:

Shakers were used for preparing the catalysts so as to ensure a thorough mixing of the substrates. Conventional filter papers proved to be unsuitable for washing as the pores blocked up too quickly. Consequently the solids were centrifuged at each washing step. The magnetic properties or the magnetic separation were tested with a commercially available magnet.

Preparation of Catalyst 7:

The preparation of Catalyst 7 is shown in FIG. 2.

1. Step: Catalyst Precursor 14

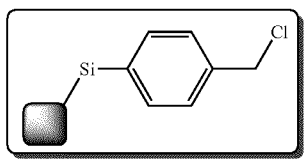

MagSilica 50/85® (15.0 g) was heated under reflux for 2 h in bidistilled H2O (150 mL) and then dried under high vacuum. The solid was suspended in toluene (180 mL) and shaken with (p-chloromethyl)phenyltrimethoxysilane (15 mL, 68.1 mmol) for 26 h. The reaction mixture was heated under reflux for 3 h. After cooling the solid was centrifuged and washed with toluene (2×40 mL). After drying under high vacuum 12.1 g of 14 were obtained as a black, magnetic powder.

2. Step: Catalyst Precursor 61

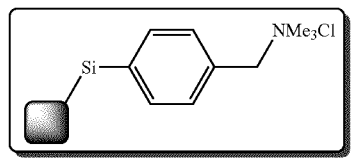

14 (12.0 g) was suspended in a toluene solution (350 mL) saturated with trimethylamine and shaken for 72 h. The solid was centrifuged and washed with toluene (3×40 mL) and dried under high vacuum. 12.4 g of 61 were obtained as a black, magnetic powder.

3. Step: Catalyst Precursor 15

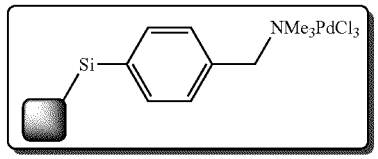

61 (3.0 g) was suspended in bidistilled H2O (150 mL) and shaken with a solution of sodium tetrachloropalladate (100 mg, 0.34 mmol) in bidistilled H2O (10 mL) for 18 h. The solid was centrifuged and washed with bidistilled H2O (2×40 mL) and dried under high vacuum. 2.7 g of 15 were obtained as a black, magnetic powder.

4. Step: Catalyst Precursor 7

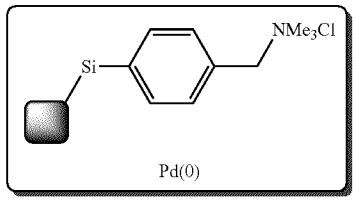

15 (2.7 g) was suspended in bidistilled H2O (30 mL) and treated with a solution of sodium borohydride (0.64 g, 16.9 mmol) in bidistilled H2O (15 mL). The reaction mixture was shaken for 5 h, centrifuged and washed with bidistilled H2O, sat. NaCl solution and H2O (40 mL each) and dried under high vacuum. 2.6 g of 7 were obtained as a black, magnetic powder. The catalyst loading was $6.7 \times 10^{-5}$ mmol Pd/mg catalyst (ICP-MS trace analysis).

Preparation of Catalyst 6:

The preparation of Catalyst 6 is shown in FIG. 3.

1. Step: Catalyst Precursor 12

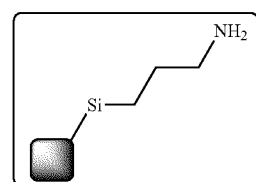

MagSilica 50/85® (6.0 g) was dried at 200° C. for 6 h under high vacuum and then suspended in abs. toluene (150 mL) in an inert gas atmosphere. 3-Aminopropyltrimethoxysilane (4.5 mL, 25.3 mmol) in abs. toluene (10 mL) was added. The reaction mixture was shaken for 16 h and centrifuged. The solid was washed with abs. toluene (2×40 mL) and aqueous toluene (1×40 mL) and then dried under high vacuum. 5.3 g of 12 were obtained as a black, magnetic powder.

2. Step: Catalyst Precursor 62

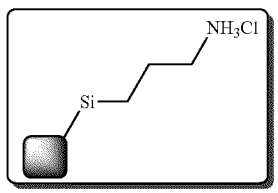

In an inert gas atmosphere 12 (4.0 g) was suspended in abs. diethyl ether (180 mL) and treated with HBF4 OEt2 (10 mL, 38.9 mmol). The reaction mixture was shaken for 2 h. The solid was then centrifuged and washed with diethyl ether, aqueous diethyl ether, sat. NaCl solution and bidistilled H2O (40 mL of each) and dried under high vacuum. 3.5 g of 62 were obtained as a black, magnetic powder.

3. Step: Catalyst Precursor 13

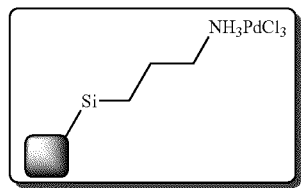

62 (3.0 g) was suspended in bidistilled H2O (150 mL) and treated with sodium tetrachloropalladate (0.5 g, 1.7 mmol) in bidistilled H2O (10 mL). The reaction mixture was shaken for 12 h. The solid was washed with bidistilled H2O until the solution was only weakly yellowish (3×40 mL) and then dried under high vacuum. 2.8 g of 13 were obtained as a black, magnetic powder. The catalyst loading was 3.7×10-5 mmol Pd/mg catalyst (ICP-MS trace analysis).

4. Step: Catalyst Precursor 6

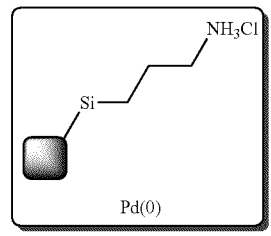

13 (2.5 g) was suspended in bidistilled H2O (40 mL) and treated with a solution of sodium borohydride (0.64 g, 16.9 mmol) in bidistilled H2O (15 mL). The reaction mixture was shaken until the evolution of gas ceased. The solid was washed with bidistilled H2O, saturated NaCl solution and bidistilled H2O (40 mL each) and dried under high vacuum. 2.3 g of 6 were obtained as a black, magnetic powder. The catalyst loading was 3.7×10-5 mmol Pd/mg catalyst.

Catalyst 8

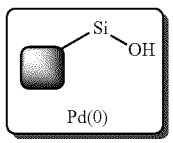

MagSilica 50/85® (2.0 g) was suspended in EtOH and stirred with a solution of palladium nitrate dihydrate (84 mg, 0.32 mmol) in EtOH (10 mL) at 50° C. for 30 min. The reaction mixture was concentrated under vacuum until dry. After drying under vacuum, 1.92 g of 8 were obtained as a black, magnetic powder. The catalyst loading was 11.3×10-5 mmol Pd/mg catalyst.

Preparation of Catalyst 9:

The preparation of Catalyst 9 is shown in FIG. 4.

1. Step: Catalyst Precursor 63

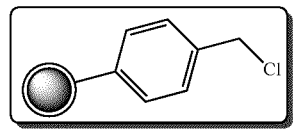

MagSilica 50/85® (3.0 g) was heated under reflux for 2 h in bidistilled H2O (50 mL) and then dried under high vacuum. The black solid in dodecane (18 mL) was treated with DVB (0.41 g, 5.3 m %), VBC (7.11 g, 94.7 m %) and AIBN (37.5 mg, 0.5 m %) and stirred with a KPG-stirrer at 70° C. for 16 h. The resulting black suspension was purified in a soxhlet extraction unit for 13 h with chloroform. The product was separated from the residual polymer and dried under high vacuum. 4.4 g of 63 were obtained as a black-greenish, magnetic powder.

2. Step: Catalyst Precursor 64

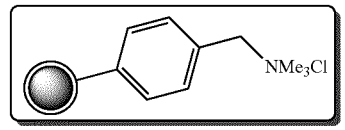

63 (4.4 g) was suspended in a toluene solution (350 mL) saturated with trimethylamine and shaken for 93 h. The solid was centrifuged and washed with toluene (3×40 mL). After drying under high vacuum a black-greenish, magnetic powder was obtained. 4.1 g of 63 were obtained.

3. Step: Catalyst Precursor 65

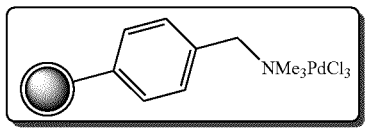

64 (4.1 g) was suspended in bidistilled H2O (150 mL) and shaken with a solution of sodium tetrachloropalladate (700 mg, 2.38 mmol) in bidistilled H2O (10 mL) for 17 h. The solid was centrifuged, washed with bidistilled H2O (3×40 mL) and dried under high vacuum. A black-greenish, magnetic solid was obtained. The crude product was employed without drying in the following reaction.

4. Step: Catalyst 9

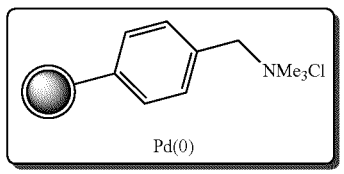

65 (4.0 g) was suspended in bidistilled H2O (50 mL) and treated with a solution of sodium borohydride (0.5 g, 13.2 mmol) in bidistilled H2O (15 mL). The reaction mixture was shaken for 2 h, centrifuged, washed with bidistilled H2O, sat. NaCl solution and H2O (40 mL each) and dried under high vacuum. 3.3 g of 9 were obtained as a black-greenish, magnetic powder.

Results of the Heating Tests:

TABLE 1

Heating Table. Measurement up to each constant temperature with 25 kHz, 2 mL/min in DMF

| PWM [‰] | Measurement time [min] | External temp. [° C.][a] | Fluid temp. [° C.] |
|---|---|---|---|
| 600 | 2 | >170 | —[c] |
| 400 | 4 | >170 | —[c] |
| 350 | 10 | >170 | 72 |
| 325 | 15 | 145 | 60 |
| 300 | 15 | 136 | 49 |
| 250 | 15 | 71 | 37 |
| 225 | 15 | 54 | 20 |
| 200 | 15 | 33 | 19 |

[a]measured with thermocouple,
[b]measured with infrared thermometer,
[c]not measured due to liquid evaporation.

Examples of Reactions:

TABLE 2

Reaction principle is shown in FIG. 5

| Ex. no. | Aryl halide | Alkene | Product | Conversion thermal [%] | Conversion inductive [%][a] |
|---|---|---|---|---|---|
| 1 | 16 | 17 | 18 | 0 | 7.5 |
| 2 | 20 | | 21 | 60.0 | 84.2 |

Heck-Mizoroki Coupling, 1 mmol aryl halide, 3 eq. Styrene, 3 eq. n-Bu3N, 2.8 mol % catalyst 7, reaction time 1 h each, flow rate 2 mL/min, PWM = 325‰.

Several chemical reactions that were carried out with the inventive process are shown below. Dimethylformamide (DMF) was used as the solvent in all cases. As a comparison, the same reactions were also carried out with conventional heating in a heated bath with the same temperatures and reaction times. The comparative reaction yields are presented in the tables, wherein "thermal" means the conversion in the heating bath (comparison) and "inductive" means the conversion after the inventive process. In the inventive process the total reaction time was attained in that the reaction medium was circulated and accordingly flowed frequently through the reactor.

In order to achieve approximately the same reaction temperature in the inventive process as in the thermal process, preliminary experiments for the heating behavior were carried out. For this, DMF was passed through a mixture of MagSilica® and sand (ca. 67 vol.% MagSilica® and 33 vol.% sand) in the tubular reactor. The inductor was always operated at 25 kHz. These conditions were also adhered to for the individual reactions.

TABLE 3

Suzuki-Miyaura Reaction is shown in FIG. 6

| Catalyst | Ex. no. | Conversion thermal [%] | Conversion inductive [%] |
|---|---|---|---|
| Najara-Katalysator[o] | 3 | 23.0 | 49.1 |
| 5% Pd/Aktivkohle[o] | 4 | 5.8 | 58.6 |
| Raschig-Ring- | 5 | 50.2 | 78.7 |

TABLE 3-continued

Suzuki-Miyaura Reaction is shown in FIG. 6

| Catalyst | Ex. no. | Conversion thermal [%] | Conversion inductive [%] |
|---|---|---|---|
| Katasylator° 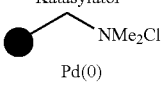 NMe₂Cl Pd(0) | | | |
| Katalysator 8° Si-OH Pd(0) | 6 | — | 97.4 |

Additional catalysts;
Suzuki-Miyaura Reaction 2 mL/min, reaction time each 1 h,: 0.5 mmol Aryl halide, 1.5 eq. boronic acid, 2.4 eq. CsF, PWM 750‰
[a]1 mol %,
[b]2.8 mol %,.

Example 7

Transesterification of ethyl cinnamate 59 to methyl cinnamate 60. This experiment was carried out following method of the literature (K. Jansson, T. Fristedt, A. Olsson, B. Svensson, S. Masson, J. Org. Chem., 2006, 71, 1658-1667). An excess of sodium methanolate was used in order to shift the transesterification equilibrium to the desired product. With inductive heating (flow rate: 2 mL/min, PWM=240‰) 93% product was isolated after 25 min. The Transesterification of ethyl cinnamate 59 to methyl cinnamate 60 is shown in FIG. 7.

Additional flow-through thermal reactions with inductive heating (prom=PWM in ‰. The numbers in % below the product formula state the product yield.)

Example 8

Syntheses of Heterocycles is shown in FIG. 8.

Example 9

Hartwig-Buchwald Coupling is shown in FIG. 9.

Example 10

Claissen Rearrangement is shown in FIG. 10.

Example 11

Decarboxylation is shown in FIG. 11.
(PH 343-48 states the batch number of the MagSilica®.)

Example 12

Hydrogenation is shown in FIG. 12.

Example 13

Reduction is shown in FIG. 13.
In examples 12 and 13 the Pd/C catalyst (palladium on active carbon) was employed in a mixture with MagSilica®. Cyclohexene essentially served as the reducing agent (hydrogen source).

Example 14

Rearrangement with C—C bond formation is shown in FIG. 14.

The invention claimed is:
1. A process for producing a target compound by a chemical reaction, the chemical reaction thermally induced by electromagnetic induction, the process comprising:
  (i) providing a liquid reaction medium comprising a plurality of different carbon-containing reactant molecules;
  (ii) disposing a heating medium comprising particles of electrically conductive and/or magnetizable solids into the reaction medium, such that the heating medium is in contact with and surrounded by the reaction medium, wherein the heating medium particles include particles having a magnetizable core surrounded by a non-magnetic Si containing shell having a moiety selected from -phenyl-CH₂—NMe₃Cl, -phenyl-CH₂—Cl, -phenyl-CH₂—NMe₃PdCl, —(CH₂)₂—NH₃Cl, —(CH₂)₂—NH₂, —(CH₂)₃—NH₃PdCl₃, —(CH₂)₃—NH₃Cl, and combinations thereof bonded thereto;
  (iii) subjecting the heating medium to an alternating field with a frequency in the range of 1 to 100 kHz to cause the heating medium to heat by electromagnetic induction; thereby heating the reaction medium by contact with the heating medium and causing the reactant molecules to react via a reaction selected from oxidation reaction, reduction reaction, fragmentation reaction, addition reaction, cycloaddition reaction, Diels-Alder reaction, substitution reaction, aromatic substitution reaction, elimination reaction, rearrangement reaction, cross coupling reaction, metathetical reaction, reaction forming a heterocycle, reaction forming an ether, reaction forming an ester, transesterification reaction, reaction forming an amine, reaction forming an amide, reaction forming an urethane, pericyclic reaction, Michael addition reaction, condensation reaction, polymerization reaction and polymer grafting reaction, and form chemical bonds between carbon atoms of different reactant molecules creating the target compound wherein there is no chemical bond formed between the reactant molecules and the heating medium particles; and
  (iv) separating the target compound from the reaction medium and the heating medium particles.
2. The process according to claim 1 in which the mean particle size of the heating medium particles is between 1 and 1000 nm.
3. The process according to claim 2 in which the heating medium further comprises additional heating medium particles having at least one core of a magnetizable material that is encapsulated by a non-magnetic material.
4. The process according to claim 1 in which the heating medium further comprises additional heating medium particles that are surface coated with a substance that is catalytically active for the chemical reaction.
5. The process according to claim 1 in which the reaction medium molecules and the heating medium particles moves relative to the other during the reaction.
6. The process according to claim 1 in which the chemical reaction is carried out at a pressure greater than atmospheric pressure and under 1.5 bar.
7. The process according to claim 1 in which second reactant molecules are present, the second reactant molecules containing an atom selected from the group consisting of H, B, O, N, S, P, Si, Ge, Sn, Pb, As, Sb, Bi and halogen, and in which a chemical bond is formed between a carbon atom and an atom selected from the group consisting of H, B, O, N, S, P, Si, Ge, Sn, Pb, As, Sb, Bi and halogen.

8. The process of claim 1 wherein the heating medium further comprises additional heating medium particles having an iron oxide core surrounded by an amorphous silica matrix shell.

9. The process of claim 1 wherein the heating medium further comprises additional heating medium particles having coating of metals selected from Sm, Ce, Fe, Co, Ni, Pt, PD and combinations thereof.

10. The process of claim 1 wherein the reactant molecule is a monomer and the target compound is a polymer.

11. The process of claim 1 wherein the heating medium further comprises particles that are not heated by electromagnetic induction.

12. The process of claim 1 wherein the heating medium further comprises particles that have catalytic properties for the chemical reaction to be carried out and are not heated by electromagnetic induction.

13. The process of claim 1 wherein the reaction is selected from oxidation reaction, reduction reaction, addition reaction, Diels-Alder reaction, substitution reaction, reaction forming a heterocycle, reaction forming an ether, reaction forming an ester, transesterification reaction, reaction forming an amine, reaction forming an amide, reaction forming an urethane, pericyclic reaction, Michael addition reaction, condensation reaction, polymerization reaction and polymer grafting reaction.

14. The process of claim 1 wherein the reaction is selected from Diels-Alder reaction, reaction forming an urethane, Michael addition reaction, condensation reaction, polymerization reaction and polymer grafting reaction.

15. The process of claim 1 wherein the reaction is selected from oxidation reaction, reduction reaction, addition reaction, Diels-Alder reaction, substitution reaction, reaction forming a heterocycle, reaction forming an ether, reaction forming an ester, transesterification reaction, reaction forming an amine, reaction forming an amide, reaction forming an urethane, pericyclic reaction, Michael addition reaction, polymerization reaction and polymer grafting reaction.

* * * * *

UNITED STATES PATENT AND TRADEMARK OFFICE
CERTIFICATE OF CORRECTION

PATENT NO. : 8,871,964 B2  
APPLICATION NO. : 13/447498  
DATED : October 28, 2014  
INVENTOR(S) : Carsten Friese et al.

Page 1 of 1

It is certified that error appears in the above-identified patent and that said Letters Patent is hereby corrected as shown below:

In the Specification

Column 4, Line 60: Change "and" to -- und --.  
Column 16, Line 56 (table 3) Fig 6: Change "Najara" to -- Najera --.  
Column 16, Line 64 (table 3) Fig 6: Change "58.6" to -- 58.8 --.  
Column 17, Line 7 (table 3): Change "Katasylator" to -- Katalysator --.  
Column 17, Line 27: Change "Masson" to -- Jönsson --.

Signed and Sealed this  
Thirtieth Day of May, 2017

Michelle K. Lee  
*Director of the United States Patent and Trademark Office*